(12) United States Patent
Sugiura (10) Patent No.: US 8,909,321 B2
(45) Date of Patent: Dec. 9, 2014

(54) DIAGNOSTIC IMAGING APPARATUS, MAGNETIC RESONANCE IMAGING APPARATUS, AND X-RAY CT APPARATUS (75) Inventor: Satoshi Sugiura, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 920 days.

(21) Appl. No.: 12/277,441

(22) Filed: Nov. 25, 2008

(65) Prior Publication Data

US 2009/0149734 A1 Jun. 11, 2009

(30) Foreign Application Priority Data

Dec. 7, 2007 (JP) .................................. 2007-317613
Oct. 22, 2008 (JP) .................................. 2008-272448

(51) Int. Cl.
A61B 5/05 (2006.01)
G01V 3/00 (2006.01)
G01R 33/567 (2006.01)
G01R 33/563 (2006.01)
G01R 33/54 (2006.01)
A61B 5/055 (2006.01)
A61B 6/00 (2006.01)
A61B 5/024 (2006.01)

(52) U.S. Cl.
CPC ............ *A61B 5/055* (2013.01); *G01R 33/5676* (2013.01); *A61B 6/503* (2013.01); *G01R 33/56325* (2013.01); *G01R 33/543* (2013.01); *G01R 33/5635* (2013.01); *A61B 6/504* (2013.01); *A61B 5/024* (2013.01); *G01R 33/56366* (2013.01); *G01R 33/546* (2013.01)
USPC .......................................... 600/413; 324/307

(58) Field of Classification Search
USPC .......... 600/410–411, 442, 456; 378/8, 87, 64, 378/62; 382/128, 131; 324/307
See application file for complete search history.

(56) References Cited

U.S. PATENT DOCUMENTS 5,871,019 A * 2/1999 Belohlavek ................... 600/450
6,426,990 B1 7/2002 Cesmeli (Continued)

FOREIGN PATENT DOCUMENTS

JP H06-20446 3/1994
JP 2000-262519 9/2000

(Continued)

OTHER PUBLICATIONS

Matthias Stuber et al, "Submillimeter Three-dimensional Coronary MR Angiorgraphy with Real-time Navigator Correction: Comparison of Navigator Locations", Radiology, vol. 212, No. 2, 1999, pp. 579-587.

(Continued)

*Primary Examiner* — Michael Rozanski
*Assistant Examiner* — Lawrence Laryea
(74) *Attorney, Agent, or Firm* — Oblon, Spivak, McClelland, Maier & Neustadt, L.L.P.

(57) ABSTRACT

A diagnostic imaging apparatus includes a ventricular volume-variation measuring unit that measures sequential variations in a size of a ventricle within at least one heart beat, from images of a heart scanned in each of a plurality of time phases; a scanning-condition setting unit that specifies a time phase of little cardiac motion based on variations in the size of the ventricle measured by the ventricular volume-variation measuring unit, and sets scanning conditions so as to collect data in the specified time phase; and an imaging unit that collects data based on the scanning conditions set by the scanning-condition setting unit, and reconstructs an image from the collected data.

25 Claims, 7 Drawing Sheets (56) References Cited

U.S. PATENT DOCUMENTS

| | | | |
|---|---|---|---|
| 6,628,743 B1* | 9/2003 | Drummond et al. | 378/8 |
| 7,175,598 B2 | 2/2007 | Yoneyama | |
| 7,877,130 B2* | 1/2011 | O'Donnell et al. | 600/410 |
| 2003/0069494 A1* | 4/2003 | Jolly | 600/410 |
| 2004/0044283 A1* | 3/2004 | Yoneyama | 600/437 |
| 2004/0073105 A1* | 4/2004 | Hamilton et al. | 600/410 |
| 2005/0152836 A1* | 7/2005 | Ashley et al. | 424/1.49 |
| 2006/0133564 A1* | 6/2006 | Langan et al. | 378/8 |
| 2006/0241376 A1* | 10/2006 | Noble et al. | 600/410 |
| 2007/0053482 A1* | 3/2007 | Kohler et al. | 378/8 |
| 2007/0053483 A1* | 3/2007 | Nagata et al. | 378/8 |
| 2007/0083105 A1* | 4/2007 | Miyazaki et al. | 600/410 |
| 2008/0077013 A1* | 3/2008 | Kawagishi et al. | 600/443 |
| 2008/0108894 A1* | 5/2008 | Elgavish et al. | 600/420 |
| 2008/0170654 A1* | 7/2008 | Tkaczyk et al. | 378/8 |
| 2009/0093707 A1* | 4/2009 | Maier | 600/410 |

FOREIGN PATENT DOCUMENTS

| | | |
|---|---|---|
| JP | 2002-530141 | 9/2002 |
| JP | 2004-500176 | 1/2004 |
| JP | 2004-509686 A | 4/2004 |
| JP | 3668629 | 4/2005 |
| JP | 2005-270491 | 10/2005 |
| JP | 2005-305151 A | 11/2005 |
| JP | 2006-524092 | 10/2006 |
| JP | 2007-068726 | 3/2007 |
| JP | 2008-125986 | 6/2008 |
| WO | WO 00/30539 A1 | 6/2000 |
| WO | WO 01/43642 A3 | 6/2001 |
| WO | WO 2004/097720 A1 | 11/2004 |

OTHER PUBLICATIONS

Sven Plein et al, "Three-Diminsional Coronary MR Angiography Performed with Subject-Specific Cardiac Acquisition Windows and Motion-Adapted Respiratory Gating", American Journal of Rentgenology, AJR:180, Feb. 2003, pp. 505-512.

Office Action issued Sep. 24, 2013 in Japanese Patent Application No. 2008-272448 with English language translation.

Japanese Office Action issued May 27, 2014, in Patent Application No. 2008-272448 with English translation.

* cited by examiner

LEFT-VENTRICULAR
SHORT AXIS CINE IMAGES

DIAGNOSTIC IMAGING APPARATUS, MAGNETIC RESONANCE IMAGING APPARATUS, AND X-RAY CT APPARATUS

CROSS-REFERENCE TO RELATED APPLICATIONS

This application is based upon and claims the benefit of priority from the prior Japanese Patent Application No. 2007-317613, filed on Dec. 7, 2007, and No. 2008-272448, filed on Oct. 22, 2008; the entire contents of which are incorporated herein by reference.

BACKGROUND OF THE INVENTION

1. Field of the Invention

The present invention relates to a diagnostic imaging apparatus, a magnetic resonance imaging apparatus, and an X-ray Computed Tomography (CT) apparatus each of which performs a scan by setting scanning conditions so as to collect data synchronously with a cardiac waveform of a subject. The present invention particularly relates to a technology for determining timing of little cardiac motion automatically without additional special scan or operator's determination.

2. Description of the Related Art

Conventionally, among methods of a cardiac scan performed by a magnetic resonance imaging apparatus, particularly a scan that requires a high spatial resolution, for example, coronary angiography, there has been a method of selectively collecting data in a time phase of little cardiac beat within a cardiac cycle for suppressing degradation in image quality due to cardiac motion (for example, see Stuber M, et al. "Submillimeter Three-dimensional Coronary MR Angiography with Real-Time Navigator Correction: Comparison of Navigator Locations", Radiology 1999; 212: 579-587). According to the method, a scan is performed by setting a predetermined delay time and a predetermined data-collection period (window), and it is known that such delay time and a period of little cardiac beat depend on beats per minute of a patient.

To ensure image quality of a cardiac scan, particularly coronary angiography, a method of performing a scan is proposed such that, for example, a cine scan for a short time adequate to recognize motion of a subject artery is preliminarily performed, an operator visually determines a period of little cardiac beat, and then the scan is performed by setting such period with respect to each patient (for example, see Plein S, et al. "Three-Dimensional Coronary MR Angiography Performed with Subject-Specific Cardiac Acquisition Window and Motion-adopted Respiratory Gating." AJR 2003; 180: 505-512).

However, according to the conventional methods described above, apart from a series of examinations, an additional cine scan of a cross section on which a coronary artery is to be visualized needs to be performed by newly performing positioning, and furthermore, the operator needs to set timing of a scan visually. For this reason, according to the conventional methods, an examination time may be sometimes extended, so that burdens to an operator and a patient are increased; and image quality may be unstable in some cases due to variations in scan timing performed by an operator.

SUMMARY OF THE INVENTION

According to one aspect of the present invention, a diagnostic imaging apparatus includes a ventricular volume-variation measuring unit that measures sequential variations in a size of a ventricle within at least one heart beat, from images of a heart scanned in each of a plurality of time phases; a scanning-condition setting unit that specifies a time phase of little cardiac motion based on variations in the size of the ventricle measured by the ventricular volume-variation measuring unit, and sets scanning conditions so as to collect data in the specified time phase; and an imaging unit that collects data based on the scanning conditions set by the scanning-condition setting unit, and reconstructs an image from the collected data.

According to another aspect of the present invention, a magnetic resonance imaging apparatus includes a ventricular volume-variation measuring unit that measures sequential variations in a size of a ventricle within at least one heart beat, from images of a heart scanned in each of a plurality of time phases; a scanning-condition setting unit that specifies a time phase of little cardiac motion based on variations in the size of the ventricle measured by the ventricular volume-variation measuring unit, and sets scanning conditions so as to collect data in the specified time phase; and an imaging unit that collects data based on the scanning conditions set by the scanning-condition setting unit, and reconstructs an image from the collected data.

According to still another aspect of the present invention, an X-ray Computed Tomography (CT) apparatus includes a ventricular volume-variation measuring unit that measures sequential variations in a size of a ventricle within at least one heart beat, from images of a heart scanned in each of a plurality of time phases; a scanning-condition setting unit that specifies a time phase of little cardiac motion based on variations in the size of the ventricle measured by the ventricular volume-variation measuring unit, and sets scanning conditions so as to collect data in the specified time phase; and an imaging unit that collects data based on the scanning conditions set by the scanning-condition setting unit, and reconstructs an image from the collected data.

DETAILED DESCRIPTION OF THE INVENTION

Exemplary embodiments of a diagnostic imaging apparatus, a magnetic resonance imaging apparatus, and an X-ray Computed Tomography (CT) apparatus according to the present invention will be explained below in detail with reference to the accompanying drawings. A magnetic resonance imaging apparatus is referred to as an MRI apparatus in the following embodiments.

Prior to explanations of an MRI apparatus according to a first embodiment of the present invention, a method of data collection and a flow of a conventional cardiac Magnetic Resonance (MR) examination performed by a conventional MRI apparatus are explained below.

Figure 1:
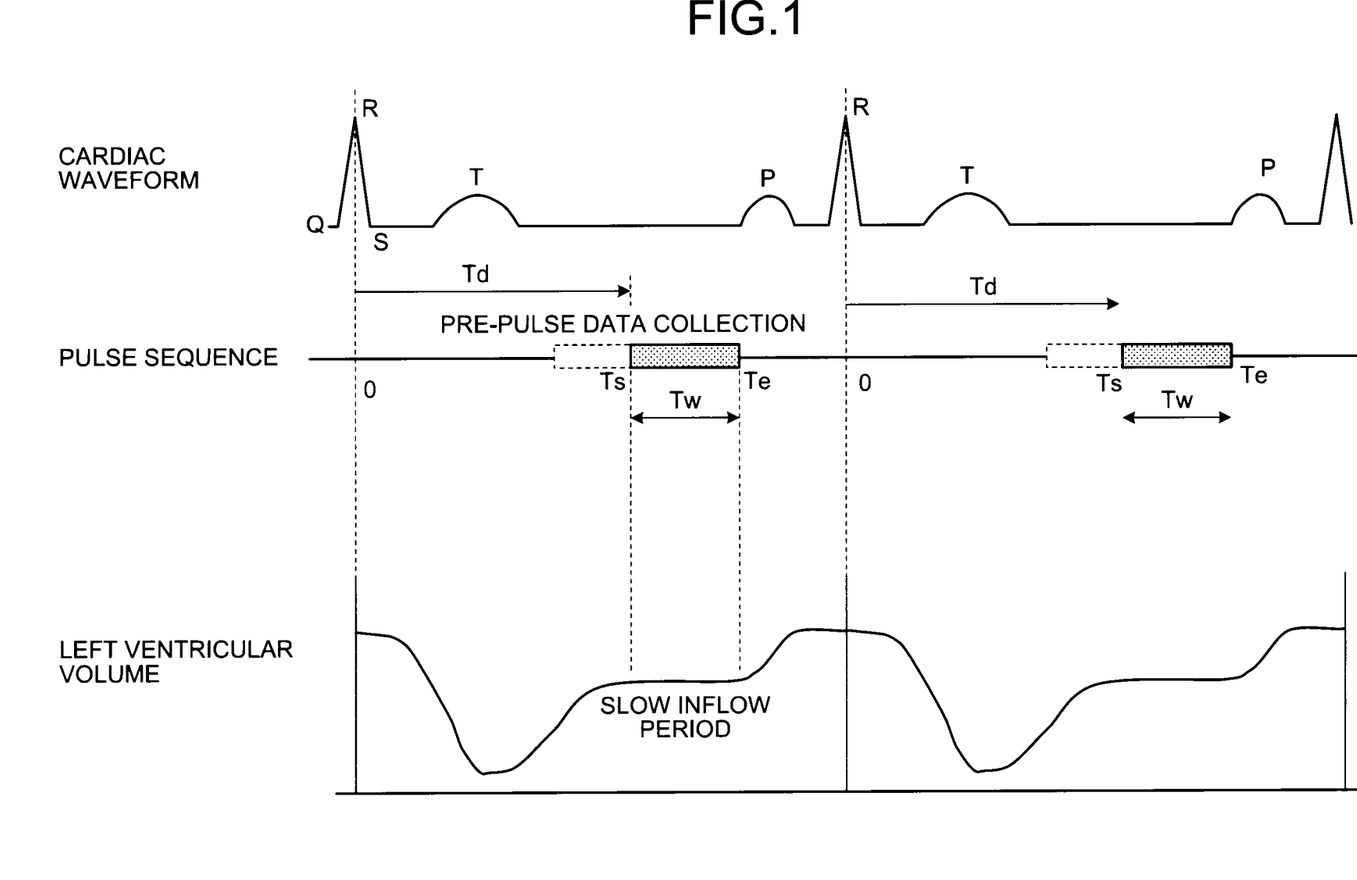
FIG. 1 is a schematic diagram for explaining a data collection method performed by a conventional Magnetic Resonance Imaging (MRI) apparatus.

First of all, a data collection method performed by the conventional MRI apparatus is explained below. FIG. 1 is a schematic diagram for explaining a data collection method performed by the conventional MRI apparatus. FIG. 1 depicts an example of a scanning method performed by an MRI apparatus for collecting data in a specific cardiac time phase in a cardiac cycle represented by coronary angiography as described in Stuber M, et al. "Submillimeter Three-dimensional Coronary MR Angiography with Real-Time Navigator Correction: Comparison of Navigator Locations", Radiology 1999; 212: 579-587).

As shown with a cardiac waveform and a pulse sequence in FIG. 1, for example, the conventional MRI apparatus detects an R wave from the cardiac waveform of a subject, and starts data collection after a lapse of a certain delay time Td from the R-wave detection, thereby collecting only data in a time phase of little cardiac motion, i.e., a time phase generally called a ventricular diastole or a slow inflow period.

The left ventricular volume shown in FIG. 1 depicts change in a left ventricular volume in one cardiac cycle as an example of a physical volume associated with cardiac motion. As shown with the left ventricular volume, a flat zone of the ventricular volume corresponds to a time phase of little cardiac motion, and by collecting data during the period of the flat zone, degradation in image quality due to an influence of cardiac motion can be suppressed.

Specifically, as shown in FIG. 1, the MRI apparatus collects data from a start time Ts at which cardiac motion turns little until a time Te at which the heart starts moving again. The pulse sequence during a scan is created such that data collection is started at the time Ts based on detection of an R wave as a starting point, data is collected during a period Tw, and the data collection is terminated at the time Te, where Tw=Te−Ts. The delay time Td from the R wave is set until the time Ts, the number of data lines N available to be collected within one heart beat is N=Tw/TR, where TR denotes a repetition time of the pulse sequence.

For example, it is assumed that three-dimensional data is to be collected. It is assumed that the number of slices, i.e., the number of slice encoding Kz is 60, and the number of matrices Ky in the phase encoding direction is 120, the number of data lines required to reconstruct an image is Kz×Ky=60× 120=7200. Additionally, it is assumed that the period Te−Ts of little cardiac motion within one cardiac cycle is 100 msec, and if the repetition time TR of the pulse sequence is 5 msec, 100/5=20 lines of data can be collected in one heart beat. Consequently, the number of heart beats required to collect all data required for image reconstruction is 7200/20=360 heart beats, so that assuming one heart beat is one second, a scan is completed in 360 seconds=6 minutes.

Generally, motion caused by breath of a patient needs to be taken into account in addition to cardiac motion, so that when a process of selectively collecting data that is only slightly affected by physical motion caused by breath is combined to the above data collection method, an actual scanning time is to be extended. In a case of coronary angiography or delayed enhancement imaging of myocardium, for example, an inversion pulse for improving contrast of an image, a T2-emphasized preparation pulse, a Magnetization Transfer Contrast (MTC) pulse, a dummy shot for helping to reach a steady state, a fat suppression pulse for suppressing a fat signal, and a pulse for detecting physical motion caused by breath are prepared prior to data collection. According to FIG. 1, a preparation period for those pulses is shown as a pre-pulse.

It is known that the period of little cardiac beat from the time Ts to the time Te depends on beats per minute of a subject. A method of setting the delay time Td and the period Tw required for creating a pulse sequence with respect to each patient is proposed as a method of obtaining a stable image quality as described in Plein S, et al. "Three-Dimensional Coronary MR Angiography Performed with Subject-Specific Cardiac Acquisition Window and Motion-adopted Respiratory Gating." AJR 2003; 180: 505-512. According to the method, prior to coronary angiography, an operator collects cine images of a cross section on which cardiac motion can be visually recognized, obtains the delay time Td, the period Tw, and the number of data lines N by visually confirming a time phase of little displacement of the coronary artery, and then sets the obtained parameters as scanning parameters of a pulse sequence of a main scan for each examination.

Generally, there are few cases where coronary angiography alone is performed in a cardiac MR examination. For example, when performing an MRI examination for diagnosis of ischemic heart disease, usually during one examination, a total diagnostic imaging of a heart is performed by carrying out a combination of (1) a cine scan for evaluation of local myocardial wall motion and measurement of cardiac function, (2) a contrast-enhanced perfusion scan for evaluating blood supply to myocardium, and (3) delayed enhancement imaging of myocardium for diagnosis of cardiac infarction; and furthermore, (4) coronary angiography is additionally performed for specifying a stenotic portion in a coronary artery that may cause ischemic heart disease.

Whether coronary angiography of (4) is to be included in a series of examinations is determined in accordance with a performance of hardware and software programs of a device to be used, an examination policy of the facility, and an examination time to be spent per patient. The myocardial perfusion test of (2) is often not performed because a stress test is required, and an evaluation method of an image is not established. The delayed enhancement imaging of myocardium of (3) is sometimes not performed because the use of a contrast agent is needed, although it is not technically difficult. Compared with the above three, the cine scan of (1) is the most basic scan that is performed in substantially all cases of an MR examination of ischemic heart disease, because it does not need a contrast agent, and almost all apparatuses can easily evaluate motion of myocardium and cardiac function.

Figure 2:
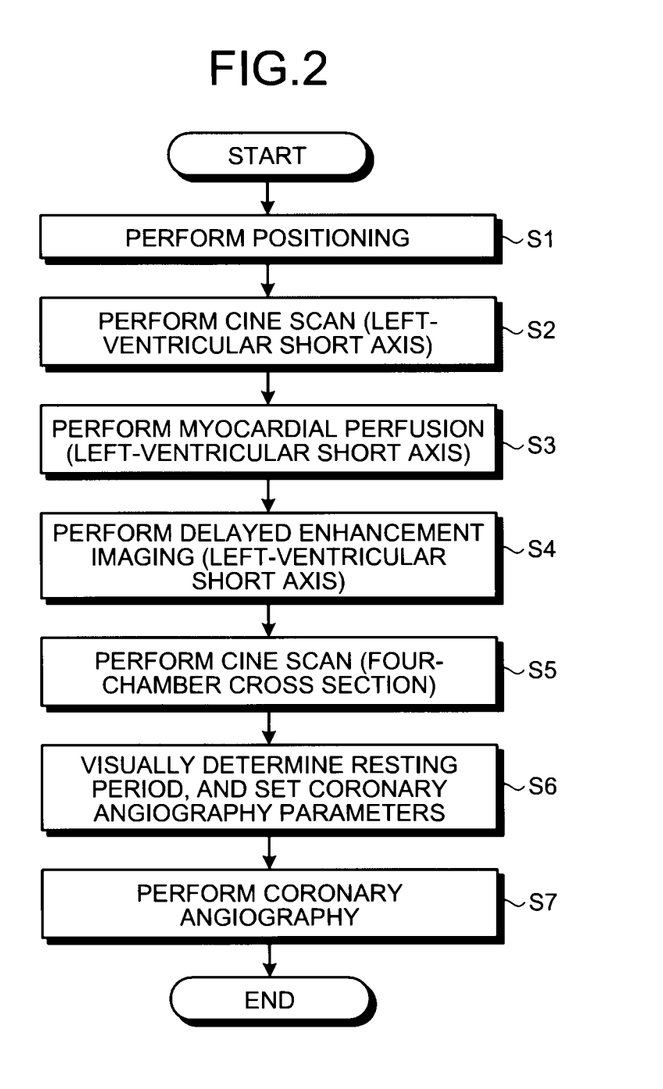
FIG. 2 is a flowchart illustrating a flow of a conventional cardiac Magnetic Resonance (MR) examination.

A flow of a conventional cardiac MR examination is explained below. FIG. 2 is a flowchart that depicts a flow of the conventional cardiac MR examination. FIG. 2 depicts an example of a series of diagnostic MR examinations of ischemic heart disease configured to perform the examinations from (1) to (4) as described above. As shown in FIG. 2, for example, to begin with, the MRI apparatus collects images for positioning (Step S1), and then scans so-called short axis slices through a cine scan corresponding to cross sections of the left ventricle from the cardiac stem to the cardiac apex (Step S2).

Subsequently, the MRI apparatus performs myocardial perfusion (Step S3), and delayed enhancement imaging (Step S4). According to the myocardial perfusion and the delayed enhancement imaging, short-axis images similar to images obtained through the cine scan are taken.

After the delayed enhancement imaging, according to the conventional examination method, before performing coronary angiography, the MRI apparatus determines the position of a four-chamber cross section on which a coronary artery can be recognized based on the short-axis images, and performs a cine scan (Step S5). An operator then visually determines a time phase of little motion of the coronary artery by causing the MRI apparatus to display scanned images sequentially and sets a delay time and a data collection time within one heart beat for the coronary angiography as scanning conditions (Step S6). The MRI apparatus then performs the coronary angiography based on the set scanning conditions (Step S7).

According to the cardiac MR examination described above, the process of setting scanning conditions (Step S6) requires operation of visual determination of a period of little positional change of an artery by comparing images in a diastole one by one from among usually 20 to 50 sheets of images in time phases; this causes the inconvenience of an extension of a time of restraint in the apparatus on a patient as the subject. Another disadvantage is that the visual determination by the operator may affect the stability of image quality of coronary angiography in some cases. Furthermore, the process requires also operation of setting scanning conditions of coronary angiography including the delay time Td and the period Tw as scanning parameters for each examination (each patient) based on an obtained result, so that the process is desired to be automated to reduce a total examination time and to ensure reconstruction performance of a coronary artery examination.

To solve such problem, instead of that an operator visually determines a period of little cardiac beat and sets scanning conditions by performing a new cine scan before performing coronary angiography as conventionally performed, according to the first embodiment, an MRI apparatus automatically sets scanning conditions based on a cine scan that is performed once in substantially all cases of a cardiac MR examination.

Specifically, the MRI apparatus according to the first embodiment measures sequential variations in the ventricular size within at least one heart beat from images (cine images) of the heart of the subject P taken in each of a plurality of time phases, specifies a time phase of little cardiac motion based on the measured variations, and sets scanning conditions based on the specified time phase.

Accordingly, according to the first embodiment, the MRI apparatus is configured to determine timing of little cardiac motion automatically without additional special scan or operator's determination.

Figure 3:
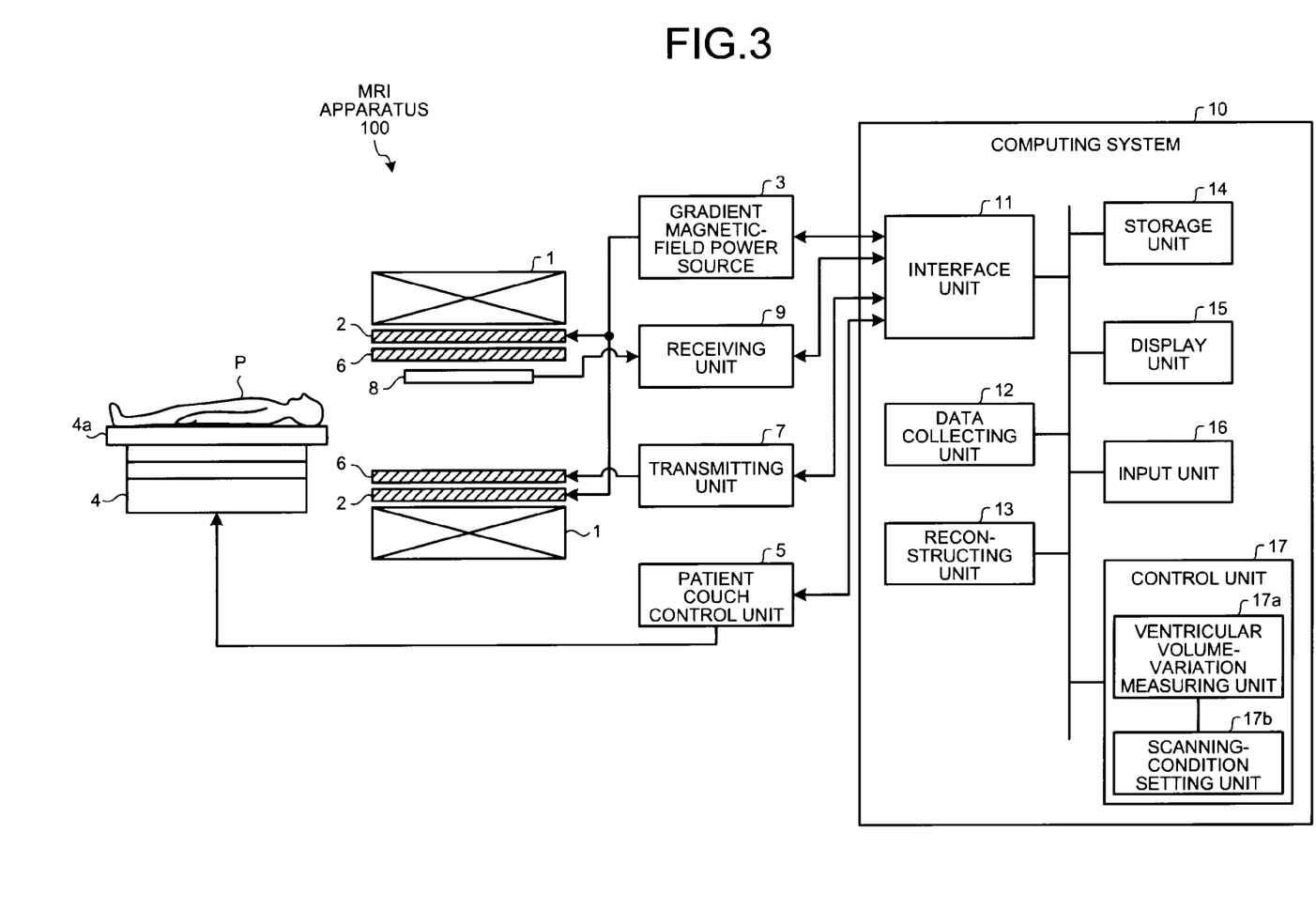
FIG. 3 is a schematic diagram illustrating a general configuration of an MRI apparatus according to a first embodiment of the present invention.

The MRI apparatus according to the first embodiment is explained below in detail. First of all, a configuration of the MRI apparatus according to the first embodiment is explained below. FIG. 3 is a schematic diagram illustrating a configuration of an MRI apparatus 100 according to the first embodiment. As shown in FIG. 3, the MRI apparatus 100 includes a static magnetic-field magnet 1, a gradient magnetic-field coil 2, a gradient magnetic-field power source 3, a patient couch 4, a patient couch control unit 5, a transmitting RF coil 6, a transmitting unit 7, a receiving Radio Frequency (RF) coil 8, a receiving unit 9, and a computing system 10.

The static magnetic-field magnet 1 is a magnet formed in a hollow cylindrical shape, and generates a uniform static magnetic field in a space its inside. For example, a permanent magnet, or a super conducting magnet is used as the static magnetic-field magnet 1.

The gradient magnetic-field coil 2 is formed in a hollow cylindrical shape, and is arranged inside the static magnetic-field magnet 1. The gradient magnetic-field coil 2 is formed of combined three coils corresponding to x, y, and z axes orthogonal to one another, and the three coils generate gradient magnetic fields along three directions of the x, y, and z axes by receiving a current supply individually from the gradient magnetic-field power source 3, which will be described later. For example, it is assumed that the z axis direction is the same direction as the static magnetic field.

The gradient magnetic fields of the x, y, and z axes generated by the gradient magnetic-field coil 2 correspond, for example, a slice-selective gradient magnetic field Gs, a phase encoding gradient magnetic field Ge, and a readout gradient magnetic field Gr, respectively. The slice-selective gradient magnetic field Gs is used for arbitrarily determining a scan cross section. The phase encoding gradient magnetic field Ge is used for changing a phase of a magnetic resonance signal in accordance with a spatial position. The readout gradient magnetic field Gr is used for changing the frequency of a magnetic resonance signal in accordance with a spatial position.

The gradient magnetic-field power source 3 supplies a current to the gradient magnetic-field coil 2. The patient couch 4 is a device that includes a top plate 4a on which the subject P is to be placed. Under the control of the couch control unit 5, which will be described later, the patient couch 4 inserts the top plate 4a on which the subject P is placed, into a hole (a scanning space) of the gradient magnetic-field coil 2. Usually, the patient couch 4 is placed such that the longitudinal direction of the patient couch 4 is to be parallel to the central axis of the static magnetic-field magnet 1.

The patient couch control unit 5 controls the patient couch 4, and moves the top plate 4a in the longitudinal direction and upward and downward by driving the patient couch 4. The transmitting RF coil 6 is arranged inside the gradient magnetic-field coil 2, and generates a high-frequency magnetic field by receiving supply of a high-frequency pulse from the transmitting unit 7.

The transmitting unit 7 includes an oscillating unit, a phase selecting unit, a frequency converting unit, an amplitude modulating unit, and a high-frequency power amplifying unit. The oscillating unit generates a high-frequency signal of a resonance frequency unique to a subject nucleus in the static magnetic field. The phase selecting unit selects a phase of the high-frequency signal. The frequency converting unit converts a frequency of the high-frequency signal output by the phase selecting unit. The amplitude modulating unit modulates amplitude of the high-frequency signal output by the frequency converting unit in accordance with, for example, a sinc function. The high-frequency power amplifying unit amplifies the high-frequency signal output by the amplitude modulating unit. As a result of operation performed by the above units, the transmitting unit 7 sends a high-frequency pulse corresponding to a Larmor frequency to the transmitting RF coil 6.

The receiving RF coil 8 is arranged inside the gradient magnetic-field coil 2, and receives a magnetic resonance signal irradiated from the subject P owing to an influence of the high-frequency magnetic field. The output signal received by the receiving RF coil 8 is input into the receiving unit 9. The receiving unit 9 creates magnetic resonance signal data based on the output signal from the receiving RF coil 8.

The computing system 10 performs total control of the MRI apparatus 100, data collection, and image reconstruction, and includes an interface unit 11, a data collecting unit 12, a reconstructing unit 13, a storage unit 14, a display unit 15, an input unit 16, and a control unit 17.

The interface unit 11 receives and outputs signals given and received between each of the above connected units and the computing system 10. The interface unit 11 is connected to the gradient magnetic-field power source 3, the patient couch control unit 5, the transmitting unit 7, the receiving RF coil 8, and the receiving unit 9, and the like.

The data collecting unit 12 collects a digital signal output by the receiving unit 9 via the interface unit 11. The data collecting unit 12 stores the collected digital signal, i.e., magnetic resonance signal data, into the storage unit 14.

The reconstructing unit 13 executes post-processing, i.e., reconstruction, such as a Fourier transform, on the magnetic resonance signal data stored in the storage unit 14, and creates data of a desired image inside the subject P.

The storage unit 14 stores therein the magnetic resonance signal data collected by the data collecting unit 12, and image data created by the reconstructing unit 13, with respect to each patient. For example, the storage unit 14 stores therein cine images of a plurality of slices taken through a cine scan.

The display unit 15 displays thereon various information, such as image data, under the control of the control unit 17. A display device, such as a liquid crystal display, can be used as the display unit 15.

The input unit 16 receives various instructions and information input from an operator. As the input unit 16, input devices, for example, pointing devices, such as a mouse or a trackball, a selecting device, such as a mode switch, and a keyboard, can be used as required.

The control unit 17 includes a Central Processing Unit (CPU) and a memory, both of which are not shown, and totally controls the MRI apparatus 100 according to the first embodiment. For example, the control unit 17 controls the MRI apparatus 100 to perform a cardiac scan synchronously to a cardiac waveform by activating each unit based on scanning conditions set by an operator or a scanning-condition setting unit 17b, which will be described later. The control unit 17 includes a ventricular volume-variation measuring unit 17a and the scanning-condition setting unit 17b as functional units related to the cardiac scan.

The ventricular volume-variation measuring unit 17a measures sequential variations in the ventricular size within at least one heart beat from images of the heart of the subject P taken in each of time phases. Specifically, to begin with, the ventricular volume-variation measuring unit 17a reads left-ventricular short-axis cine images sequentially taken in each of time phases from the storage unit 14, and automatically extracts myocardial contours from the read cine images.

When automatically extracting myocardial contours, the ventricular volume-variation measuring unit 17a uses a known method, for example, a method disclosed in Japanese Patent No. 3668629. Particularly cine images are usually collected in accordance with a Steady State Free Precession (SSFP). Contours can be easily extracted automatically because this method enhances contrast between myocardium and intracardiac blood.

Figure 4:
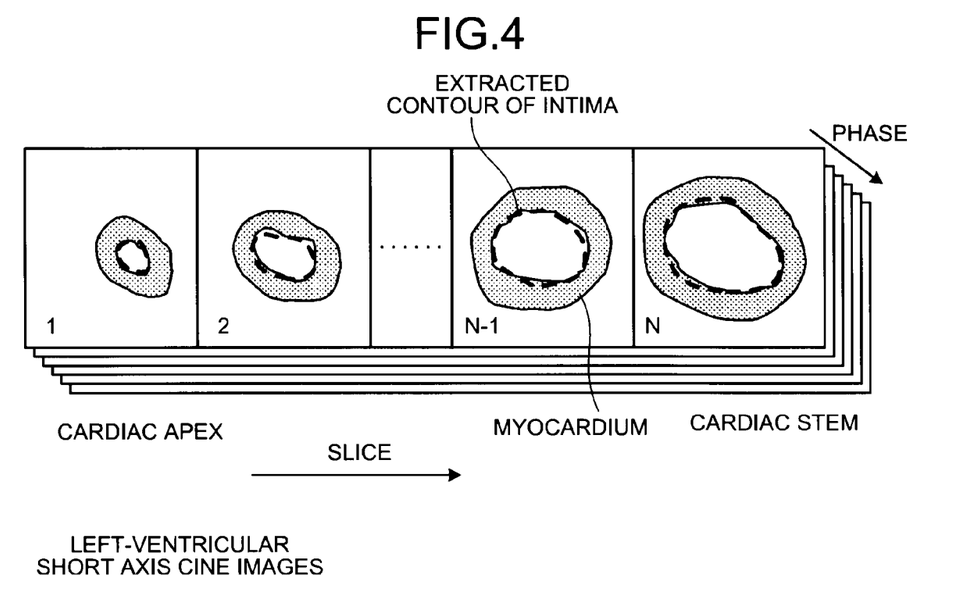
FIG. 4 is a schematic diagram for explaining contour extraction performed by a ventricular volume-variation measuring unit.

FIG. 4 is a schematic diagram for explaining contour extraction performed by the ventricular volume-variation measuring unit 17a. FIG. 4 depicts cine images in time phases of slices from the cardiac apex to the cardiac stem of the left ventricle (1 to N shown in FIG. 4), and contours of myocardial intima of the left ventricle extracted according to the above method. As shown in FIG. 4, the ventricular volume-variation measuring unit 17a extracts contours of the myocardial intima from all of the images of the left ventricle of the slices and the time phases.

Subsequently, the ventricular volume-variation measuring unit 17a calculates an area inside the intima contour, and calculates a left ventricular volume per slice by multiplying the calculated area by a slice thickness, with respect to each of the slices in one time phase. The ventricular volume-variation measuring unit 17a then calculates a left ventricular volume in the time phase by summing all of the calculated values of the left ventricular volume per slice.

Figure 5:
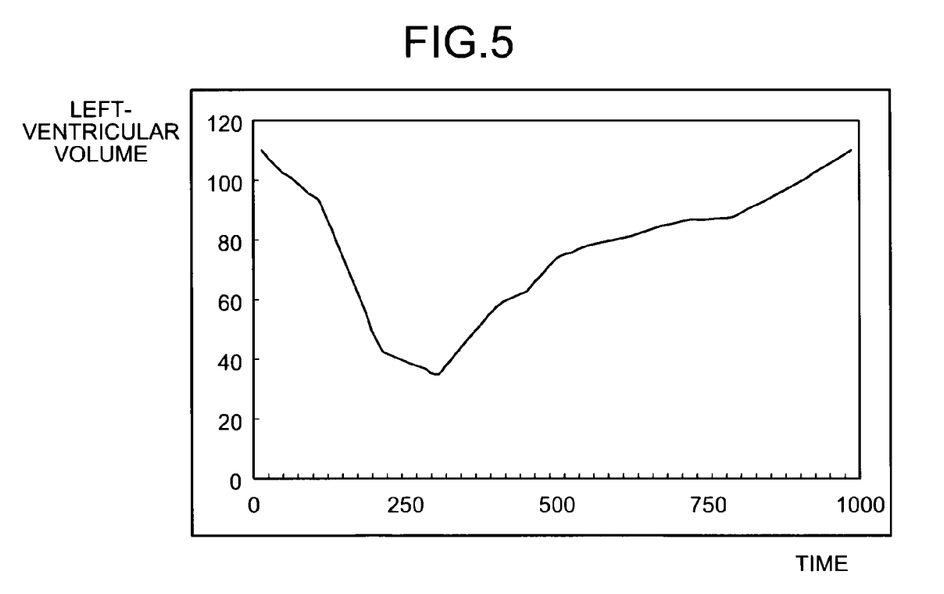
FIG. 5 is a schematic diagram illustrating a relation between time phases and left ventricular volumes obtained by the ventricular volume-variation measuring unit.

The ventricular volume-variation measuring unit 17a then creates information indicating relation between the time phases and the left ventricular volumes by performing the above-explained calculation of the left ventricular volume with respect to each of the time phases. FIG. 5 is a schematic diagram that depicts relation between the time phases and the left ventricular volumes obtained by the ventricular volume-variation measuring unit 17a. The ventricular volume-variation measuring unit 17a creates information that indicates sequential variations in the left ventricular volume within one heart beat as shown in FIG. 5. The information is one of parameters that reflect cardiac functions, and is to be generally measured during a cardiac examination apart from an object of the first embodiment.

Figure 6:
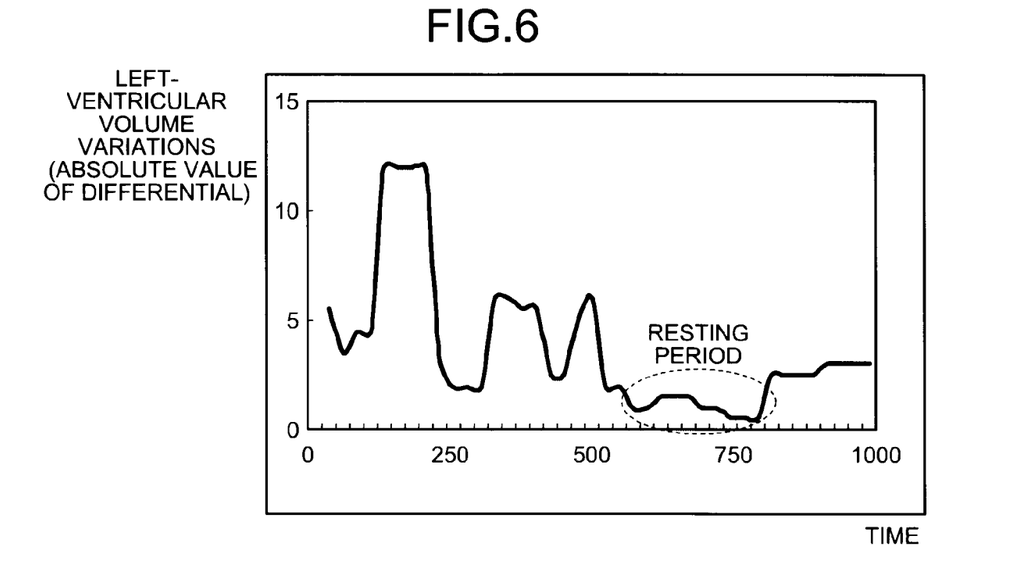
FIG. 6 is a schematic diagram illustrating a relation between the time phases and left-ventricular volume variations obtained by the ventricular volume-variation measuring unit.

Subsequently, the ventricular volume-variation measuring unit 17a creates information indicating relation between the time phases and the left-ventricular volume variations by calculating the absolute value of a differential between a left ventricular volume in the time phase and a left ventricular volume in one previous time phase, based on the information indicating the relation between the time phases and the left ventricular volumes created as described above. FIG. 6 is a schematic diagram that depicts relation between the time phases and the left-ventricular volume variations obtained by the ventricular volume-variation measuring unit 17a. The ventricular volume-variation measuring unit 17a creates information that indicates change with time in the left-ventricular volume variations within one heart beat as shown in FIG. 6.

On a curve shown in FIG. 6, a time phase of little cardiac motion is a period of little change with time in the left-ventricular volume variations (a resting period shown in FIG. 6).

The scanning-condition setting unit 17b specifies a time phase of little cardiac motion based on variations in the ventricular size measured by the ventricular volume-variation measuring unit 17a, and sets scanning conditions based on the specified time phase. Specifically, the scanning-condition setting unit 17b specifies a time phase of little cardiac motion based on information indicating relation between time phases and left-ventricular volume variations created by the ventricular volume-variation measuring unit 17a, and sets scanning conditions for a cardiac scan.

Figure 7:
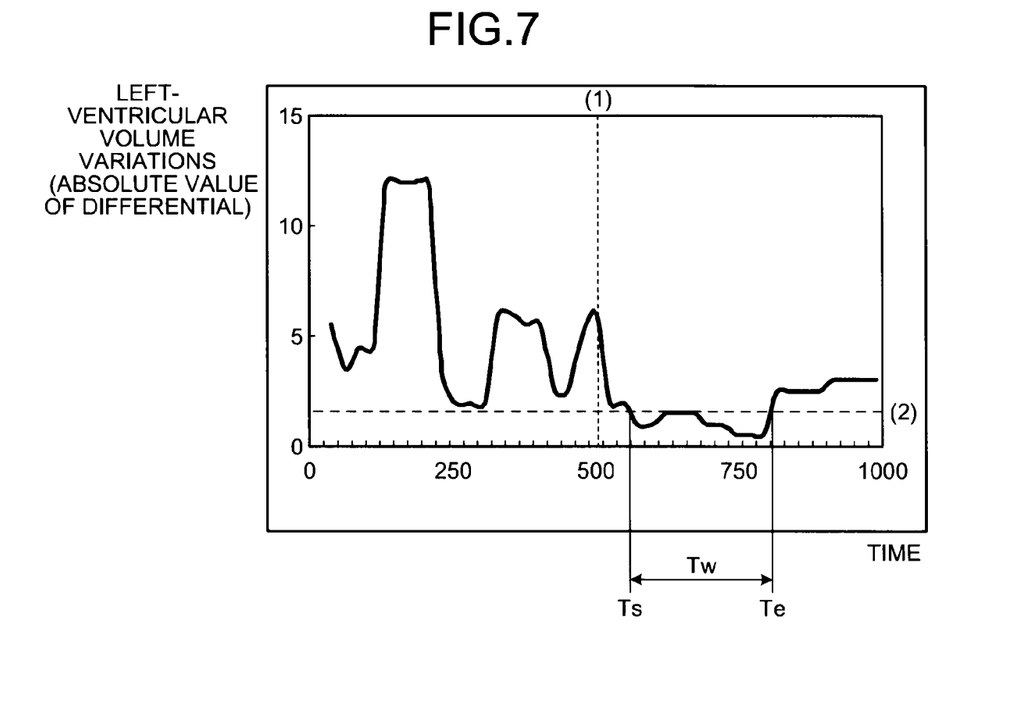
FIG. 7 is a schematic diagram for explaining operation of specifying a time phase performed by a scanning-condition setting unit.

FIG. 7 is a schematic diagram for explaining operation of specifying a time phase performed by the scanning-condition setting unit 17b. FIG. 7 depicts the relation shown in FIG. 6, which is between the time phases and the left-ventricular volume variations created by the ventricular volume-variation measuring unit 17a. For example, the scanning-condition setting unit 17b calculates respective times from an R wave corresponding to the time Ts and the time Te shown in FIG. 1 by specifying a time on a curve shown in FIG. 7 at which the left-ventricular volume variations are smaller than a predetermined value ((2) shown in FIG. 7) after a certain lapse from a starting point ((1) shown in FIG. 7).

The scanning-condition setting unit 17b then sets scanning conditions for a cardiac scan based on the time Ts and the time Te calculated by the scanning-condition setting unit 17b. For example, when performing coronary angiography, the scanning-condition setting unit 17b calculates the delay time Td from the R wave and the number of data lines N within one heart beat, both of which are required for setting scanning conditions, where Td=Ts, N=Tw/TR (Tw is calculated in accordance with Tw=Te−Ts as shown in FIG. 7), and sets scanning conditions by using the calculated values of the delay time Td and the number of data lines N.

Figure 8:
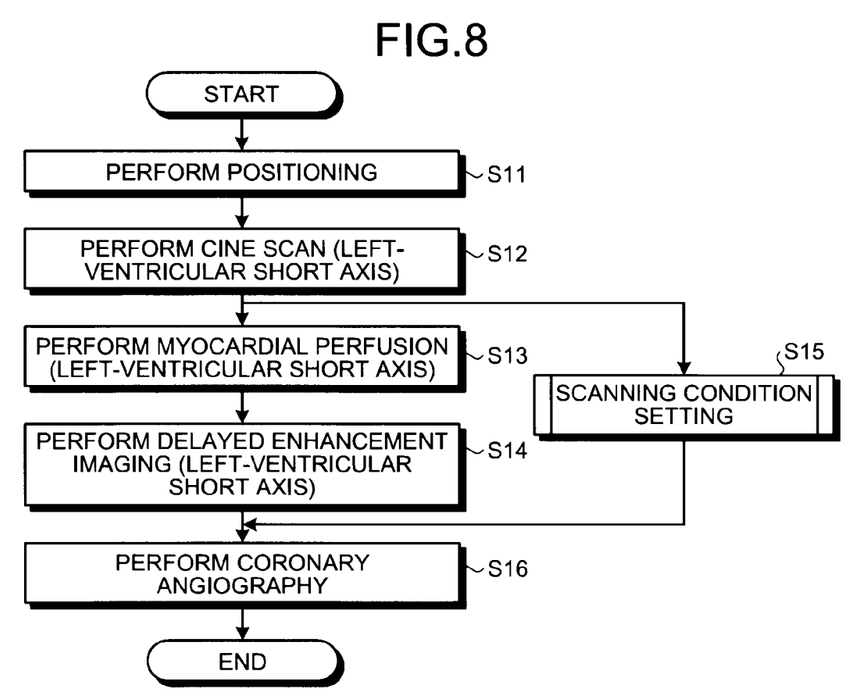
FIG. 8 is a flowchart for explaining a flow of a cardiac MR examination performed by the MRI apparatus according to the first embodiment.

A flow of a cardiac MR examination performed by the MRI apparatus 100 according to the first embodiment is explained below. FIG. 8 is a flowchart for explaining a flow of a cardiac MR examination performed by the MRI apparatus 100 according to the first embodiment. A case of performing an examination similar to the MR examination shown in FIG. 2 is explained below.

As shown in FIG. 8, according to the cardiac MR examination, to begin with, the MRI apparatus 100 according to the first embodiment collects images for positioning (Step S11), and then scans so-called short axis slices through a cine scan corresponding to cross sections of the left ventricle from the cardiac stem to the cardiac apex (Step S12).

Subsequently, the MRI apparatus 100 performs myocardial perfusion (Step S13), and delayed enhancement imaging (Step S14). According to the myocardial perfusion and the delayed enhancement imaging, short-axis images similar to images obtained through the cine scan are taken.

In parallel with the myocardial perfusion and the delayed enhancement imaging, the MRI apparatus 100 sets scanning conditions for subsequent coronary angiography (Step S15). Setting of the scanning conditions will be explained later in detail. The MRI apparatus 100 then performs coronary angiography based on the set scanning conditions (Step S16).

Figure 9:
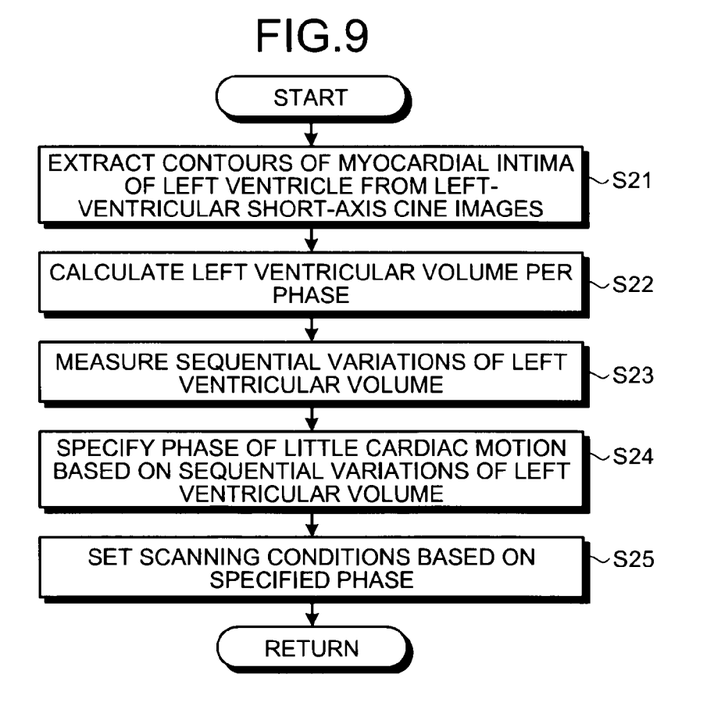
FIG. 9 is a flowchart illustrating a process procedure of the scanning-condition.

A process procedure of scanning-condition setting shown in FIG. 8 is explained below. FIG. 9 is a flowchart of a process procedure of the scanning-condition setting shown in FIG. 8. As shown in FIG. 9, according to the process procedure of the scanning-condition setting, with the computing system 10, the ventricular volume-variation measuring unit 17a extracts contours of the myocardial intima of the left ventricle from the left-ventricular short-axis cine images (Step S21), calculates a left ventricular volume per time phase (Step S22), and furthermore, measures sequential variations in the left ventricular volume (Step S23).

The scanning-condition setting unit 17b then specifies a time phase of little cardiac motion based on the sequential variations in the left ventricular volume measured by the ventricular volume-variation measuring unit 17a (Step S24), and sets scanning conditions for coronary angiography based on the specified time phase (Step S25).

In this way, instead of that the operator visually determines a period of little cardiac beat and sets scanning conditions by performing a new cine scan before performing coronary angiography as performed in the conventional cardiac MR examination shown in FIG. 2, the MRI apparatus 100 according to the first embodiment can automatically sets scanning conditions based on one cine scan that is performed once in substantially all cases of a cardiac MR examination.

As described above, according to the first embodiment, the ventricular volume-variation measuring unit 17a measures sequential variations in the ventricular size within at least one heart beat from images of the heart of the subject P taken in each of time phases. The scanning-condition setting unit 17b specifies a time phase of little cardiac motion based on variations in the ventricular size measured by the ventricular volume-variation measuring unit 17a, and sets scanning conditions based on the specified time phase. Accordingly, timing of little cardiac motion can be automatically determined without additional special scan or operator's determination.

Accordingly, for example, an additional scan for observing the motion of the coronary artery and time for positioning required for the additional scan can be omitted, and moreover, time for visually confirming a period of little motion of the coronary artery and setting scanning conditions can be omitted. In addition, by automatically setting scanning conditions, change in the image quality caused by a difference in determination operator to operator can be suppressed.

Although according to the first embodiment, a case of measuring a volume of the left ventricle by taking cardiac cine images (cine images of the heart) on slices that cover the whole of the left ventricle is explained above, the present invention is not limited to this. In other words, data of the volume is not necessarily required for an object of the present invention that is to determine a time phase of little cardiac motion automatically. For example, by creating a curve of cross-sectional area by using one or a plurality of left-ventricular short-axis cross sections, the cross-sectional area curve can be used instead of the volume curve.

Moreover, a case of performing a cine scan other than the short axis can be considered depending on an examination protocol. In such case, for example, measurement of a left-ventricular long-axis area or measurement of the left-ventricular area of a four-chamber cross section can substitute. If scanning no cine image, an area can be measured by automatic contour extraction by scanning one left-ventricular short-axis cross section prior to coronary angiography. In such case, an additional special scan of one slice needs to be performed for setting scanning conditions for the coronary angiography; however, compared with the conventional visual determination, improvements in examination time and reconstruction performance of a scan can be obtained.

Although according to the first embodiment, a case of setting scanning conditions for coronary angiography is explained above, the present invention is not limited to this, and can be similarly applied to a case of setting scanning conditions for other scans that collect data synchronously with a cardiac waveform. As a scan that collects data synchronously with a cardiac waveform, for example, there is angiography without contrast agent called Fresh Blood Imaging (FBI).

According to FBI, to begin with, the MRI apparatus collects data in time phases on the same slice, and performs a preparatory scan for taking a plurality of images in different time phases. The MRI apparatus then determines appropriate time phases in a systole and a diastole from the scanned images, and takes images in the systole and images in the diastole. By creating differential images obtained in this way, an image of an artery and an image of a vein can be separately created. According to the FBI, by applying the present invention to the preparatory scan described above, examination time of the FBI can be reduced, and a stable quality image of a blood vessel can be obtained.

According to the first embodiment, a case where the scanning-condition setting unit 17b specifies a time phase of little cardiac motion by using a threshold value is explained above. However, because the extent of the ventricular size variations varies among individuals; if the threshold value is a fixed value, when scanning a subject whose ventricular size variations are larger than a standard, there is a possibility that a period during which variations fall below the threshold value may not be detected.

To solve such problem, for example, it can be configured such that the scanning-condition setting unit 17b calculates a value smaller than the maximum value of variations that indicate change in the ventricular size by multiplying the maximum value by a certain rate (for example, 10%), and then the calculated value is to be used as the threshold value. Accordingly, the threshold value changes in accordance with variations in the ventricular size, so that timing of little cardiac motion can be appropriately determined in accordance with a physical predisposition and symptoms of each subject.

Moreover, for example, when the scanning-condition setting unit 17b detects a plurality of periods during which variations indicating change in the ventricular size fall below a threshold value, the scanning-condition setting unit 17b can specify the longest period among the detected periods as a time phase of little cardiac motion. Accordingly, data can be collected in a time phase of the most stable cardiac motion, and a better quality image can be obtained.

Furthermore, when the scanning-condition setting unit 17b detects no period during which variations indicating change in the ventricular size fall below a threshold value, the scanning-condition setting unit 17b can repeat detection of a period by increasing the threshold value stepwise until one or more period is detected. In such case, for example, to begin with, the scanning-condition setting unit 17b measures the maximum value of variations in the ventricular size in a certain heart beat, and sets a threshold value to a value equivalent to 10% of the maximum value. If no period during which variations fall below the set threshold value is detected, the scanning-condition setting unit 17b then repeats setting of a threshold value stepwise by increasing the rate to the maximum value measured at first by 1% each until one or more period is detected. Accordingly, an individual difference of a subject can be more flexibly coped with.

The first embodiment is explained above in a case where the present invention is applied to an MRI apparatus. However, the present invention is not limited to this, and can be similarly applied to other diagnostic imaging apparatuses. As a second embodiment according to the present invention, a case of applying the present invention to an X-ray CT apparatus is explained below.

Figure 10:
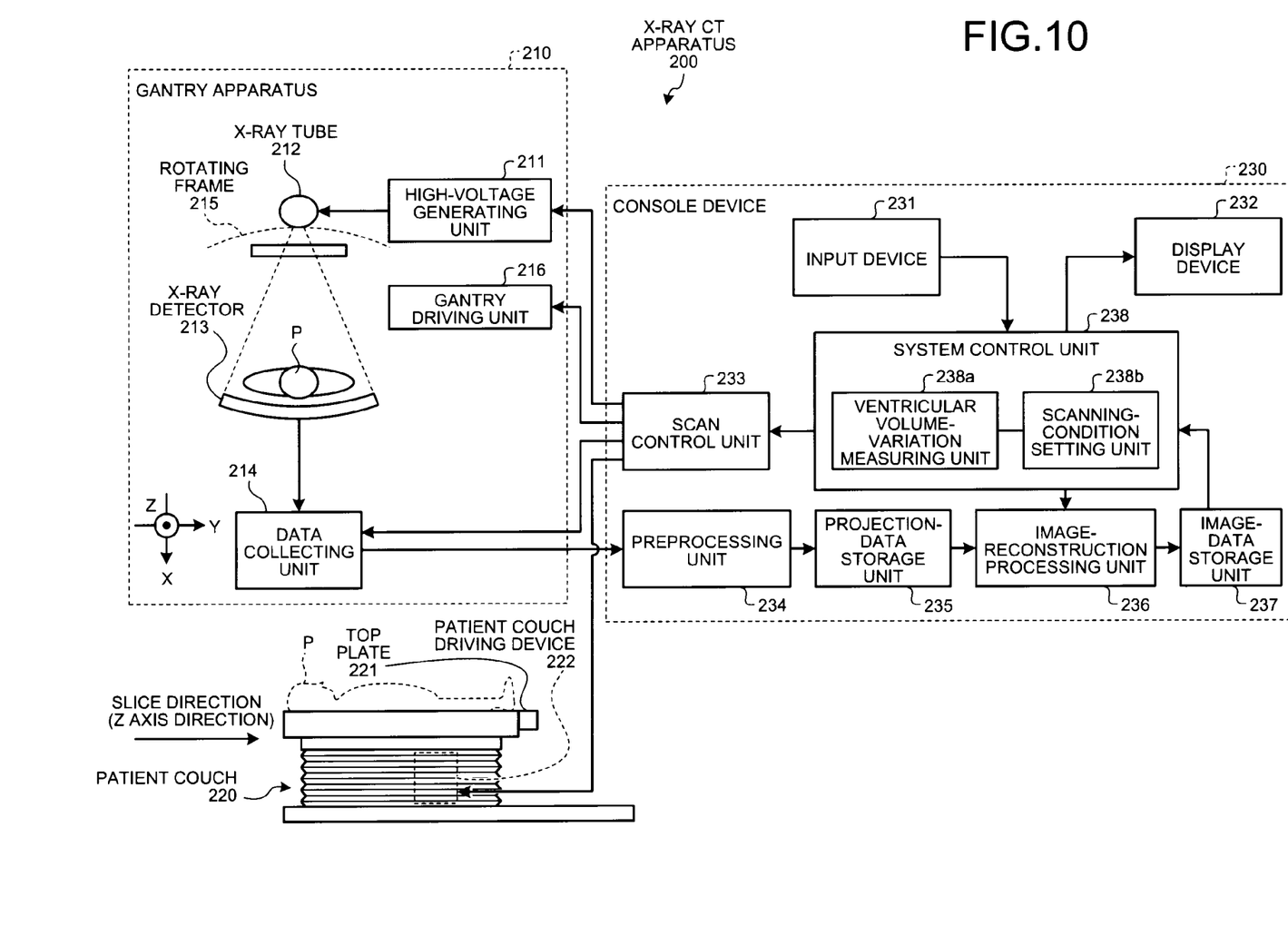
FIG. 10 is a schematic diagram illustrating a configuration of an X-ray Computed Tomography (CT) apparatus according to a second embodiment of the present invention.

FIG. 10 is a schematic diagram illustrating a configuration of an X-ray CT apparatus 200 according to the second embodiment. As shown in FIG. 10, the X-ray CT apparatus 200 includes a gantry apparatus 210, a patient couch 220, and a console device 230.

The gantry apparatus 210 collects projection data by irradiating the subject P with X-rays. The gantry apparatus 210 includes a high-voltage generating unit 211, an X-ray tube 212, an X-ray detector 213, a data collecting unit 214, a rotating frame 215, and a gantry driving unit 216.

The high-voltage generating unit 211 supplies a high voltage to the X-ray tube 212. The X-ray tube 212 generates X-rays with a high voltage supplied by the high-voltage generating unit 211. The X-ray detector 213 detects X-rays that have passed through the subject P. The data collecting unit 214 creates projection data by using the X-rays detected by the X-ray detector 213.

The rotating frame 215 is formed in a toroidal shape, and rotates rapidly and continuously. The rotating frame 215 supports the X-ray tube 212 and the X-ray detector 213 on opposite sides of the subject P. The gantry driving unit 216 rotates the X-ray tube 212 and the X-ray detector 213 in a circular orbit of which center is the subject P by rotationally driving the rotating frame 215.

The patient couch 220 moves the subject P to a scanning position inside the gantry apparatus 210. The patient couch 220 includes a top plate 221 and a couch driving device 222. The top plate 221 is a plate on which the subject P is to be placed when performing a scan. The couch driving device 222 moves the top plate 221 to a slice direction.

The console device 230 receives various instructions related to operation of the X-ray CT apparatus 200 from an operator, and reconstructs an image from projection data collected by the gantry apparatus 210. The console device 230 includes an input device 231, a display device 232, a scan control unit 233, a preprocessing unit 234, a projection-data storage unit 235, an image-reconstruction processing unit 236, an image-data storage unit 237, and a system control unit 238.

The input device 231 includes a mouse and a keyboard, and receives an instruction to the X-ray CT apparatus 200 from the operator. For example, the input device 231 receives input of scanning conditions, and receives an instruction of the start of a scan, from the operator when scanning. The scanning conditions includes, for example, irradiation intervals of X-rays, a scanning time, a tube current to be supplied to the X-ray tube.

The display device 232 includes a display device, such as a liquid crystal display (LCD), and displays thereon various information. For example, the display device 232 displays thereon image data stored by the image-data storage unit 237, which will be described later, and a Graphical User Interface (GUI) for receiving various instructions from the operator.

Under the control of the system control unit 238, which will be described later, the scan control unit 233 irradiates the heart of the subject P with X-rays by activating the high-voltage generating unit 211, the data collecting unit 214, the gantry driving unit 216, and the couch driving device 222 based on scanning conditions instructed by the system control unit 238, and collects projection data.

The preprocessing unit 234 performs preprocessing, such as sensitivity correction, on projection data created by the data collecting unit 214. The projection-data storage unit 235 stores therein projection data preprocessed by the preprocessing unit 234. The image-reconstruction processing unit 236 reconstructs an image data from projection data stored by the projection-data storage unit 235 under the control of the system control unit 238.

The image-data storage unit 237 stores therein an image data reconstructed by the image-reconstruction processing unit 236. For example, the image-data storage unit 237 stores therein cine images of the heart of the subject P taken in each of time phases.

The system control unit 238 performs overall control of the X-ray CT apparatus 200 by controlling operation of the gantry apparatus 210, the patient couch 220, and the console device 230. According to the second embodiment, the system control unit 238 includes particularly a ventricular volume-variation measuring unit 238a and a scanning-condition setting unit 238b.

The ventricular volume-variation measuring unit 238a has a function similar to that of the ventricular volume-variation measuring unit 17a explained in the first embodiment. Specifically, the ventricular volume-variation measuring unit 238a reads left-ventricular short-axis cine images sequentially taken in each of time phases from the image-data storage unit 237, and measures sequential variations in the ventricular size based on the read cine images similarly to the ventricular volume-variation measuring unit 17a.

When measuring the sequential variations in the ventricular size, for example, the ventricular volume-variation measuring unit 238a uses, as cine images of the heart, images of the whole heart taken in a preparatory scan performed prior to a main scan by irradiating the heart with X-rays of a lower dose than that in the main scan. Alternatively, the ventricular volume-variation measuring unit 238a can use, as cine images of the heart, partial images of the heart taken in a preparatory scan performed prior to a main scan by irradiating an area narrower than that in the main scan with X-rays. In either of the cases, a dose of X-rays irradiated to the subject P through the examination can be reduced.

The scanning-condition setting unit 238b has a function similar to that of the scanning-condition setting unit 17b explained in the first embodiment. Specifically, the scanning-condition setting unit 238b specifies a time phase of little cardiac motion based on variations in the ventricular size measured by the ventricular volume-variation measuring unit 238a similarly to the scanning-condition setting unit 17b, and sets scanning conditions based on the specified time phase.

When setting the scanning conditions, the scanning-condition setting unit 238b sets scanning conditions such that a dose of X-rays to be irradiated to the subject P when collecting data in the specified time phase is to be more than that when collecting data in other time phases within one heart beat. Alternatively, the scanning-condition setting unit 238b sets scanning conditions such that a dose of X-rays to be irradiated to the subject when collecting data in other time phases in one heart beat is zero. Accordingly, a dose of X-rays irradiated to the subject P can be suppressed to the minimum quantity.

As described above, according to the second embodiment, the ventricular volume-variation measuring unit 238a measures sequential variations in the ventricular size within at least one heart beat from images of the heart of the subject P taken in each of time phases. The scanning-condition setting unit 238b specifies a time phase of little cardiac motion based on variations in the ventricular size measured by the ventricular volume-variation measuring unit 238a, and sets scanning conditions based on the specified time phase. Accordingly, similarly to the first embodiment, timing of little cardiac motion can be automatically determined without additional special scan or operator's determination.

The components of each device shown in the drawings in the above embodiments are conceptual for describing functions, and not necessarily to be physically configured as shown in the drawings. In other words, concrete forms of distribution and integration of the units are not limited to those shown in the drawings, and all or part of the units can be configured to be functionally or physically distributed and integrated per arbitrary unit depending on various loads and conditions of the use.

As described above, the diagnostic imaging apparatus, the magnetic resonance imaging apparatus, and the X-ray CT apparatus according to the embodiments of the present invention are useful for setting scanning conditions to collect data synchronously with a cardiac waveform of a subject, and suitable particularly when it is desired to reduce a total examination time and to ensure reconstruction performance of a coronary artery examination.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A diagnostic imaging apparatus, comprising:
a controller configured to
obtain, from a first preparatory scan, images of a heart in each of a plurality of time phases, and cause additional cardiac imaging to be performed after the first preparatory scan,
measure sequential variations in a size of a ventricle within at least one heart beat, from the obtained images of the heart,
specify a time phase of little cardiac motion based on variations in the size of the ventricle, set scanning conditions based on the specified time phase, detect a period during which a volume variation indicating change in the size of the ventricle falls below a threshold value, and specify the detected period as the time phase of little cardiac motion, and
set the scanning conditions based only on the images obtained from the first preparatory scan; and
an imaging unit that performs one of coronary angiography and non-contrast angiography based on the set scanning conditions,
wherein the controller is configured to cause only the first preparatory scan to be performed, without causing other preparatory scans for specifying the time phase to be performed.

2. The apparatus according to claim 1, wherein the controller is configured to calculate a volume of the ventricle as an index indicating a size of the ventricle, and measure sequential variations in the calculated volume.

3. The apparatus according to claim 2, wherein the controller is configured to calculate a value smaller than a maximum value of volume variations indicating the change in the size of the ventricle by multiplying the maximum value by a certain rate, and use the calculated value as the threshold value.

4. The apparatus according to claim 3, wherein when the controller detects a plurality of periods during which the volume variation indicating the change in the size of the ventricle falls below the threshold value, the controller is configured to specify a longest period among the detected periods as the time phase of little cardiac motion.

5. The apparatus according to claim 3, wherein when the controller detects no period during which the volume variation indicating the change in the size of the ventricle falls below the threshold value, the controller is configured to repeat detection of a period until one or more periods is detected by increasing the threshold value stepwisely.

6. The apparatus according to claim 2, wherein when the controller detects a plurality of periods during which the volume variation indicating the change in the size of the ventricle falls below the threshold value, the controller is configured to specify a longest period among the detected periods as the time phase of little cardiac motion.

7. The apparatus according to claim 2, wherein when the controller detects no period during which the volume variation indicating the change in the size of the ventricle falls below the threshold value, the controller is configured to repeat detection of a period until one or more periods is detected by increasing the threshold value stepwisely.

8. The apparatus according to claim 1, wherein the controller is configured to calculate a cross-section of the ventricle as an index indicating a size of the ventricle, and measure sequential variations in the calculated cross-section.

9. The apparatus according to claim 8, wherein the controller is configured to calculate a value smaller than a maximum value of volume variations indicating the change in the size of the ventricle by multiplying the maximum value by a certain rate, and use the calculated value as the threshold value.

10. The apparatus according to claim 8, wherein when the controller detects a plurality of periods during which the volume variation indicating the change in the size of the ventricle falls below the threshold value, the controller is configured to specify a longest period among the detected periods as the time phase of little cardiac motion.

11. The apparatus according to claim 8, wherein when the controller detects no period during which the volume variation indicating the change in the size of the ventricle falls below the threshold value, the controller is configured to repeat detection of a period until one or more periods is detected by increasing the threshold value stepwisely.

12. The apparatus according to claim 1, wherein the controller is configured to calculate a value smaller than a maximum value of volume variations indicating the change in the size of the ventricle by multiplying the maximum value by a certain rate, and use the calculated value as the threshold value.

13. The apparatus according to claim 12, wherein when the controller detects a plurality of periods during which the volume variation indicating the change in the size of the ventricle falls below the threshold value, the controller is configured to specify a longest period among the detected periods as the time phase of little cardiac motion.

14. The apparatus according to claim 12, wherein when the controller detects no period during which the volume variation indicating the change in the size of the ventricle falls below the threshold value, the controller is configured to repeat detection of a period until one or more periods is detected by increasing the threshold value stepwisely.

15. The apparatus according to claim 1, wherein when the controller detects a plurality of periods during which the volume variation indicating the change in the size of the ventricle falls below the threshold value, the controller is configured to specify a longest period among the detected periods as the time phase of little cardiac motion.

16. The apparatus according to claim 1, wherein when the controller detects no period during which the volume variation indicating the change in the size of the ventricle falls below the threshold value, the controller is configured to repeat detection of a period until one or more periods is detected by increasing the threshold value stepwisely.

17. The diagnostic imaging apparatus of claim 1, wherein the controller is configured to set the scanning conditions in parallel with the performance of the additional cardiac imaging.

18. The diagnostic imaging apparatus of claim 1, wherein the controller is configured to cause the additional cardiac imaging to be performed, the additional cardiac imaging including myocardial perfusion and delayed enhancement imaging.

19. The diagnostic imaging apparatus of claim 1, wherein the controller is configured to cause the first preparatory scan to be performed, wherein the first preparatory scan is a left-ventricular short axis cine scan.

20. A magnetic resonance imaging apparatus, comprising:
a controller configured to
obtain, from a first preparatory scan, images of a heart in each of a plurality of time phases, and cause additional cardiac imaging to be performed after the first preparatory scan,
measure sequential variations in a size of a ventricle within at least one heart beat, from the obtained images of the heart,
specify a time phase of little cardiac motion based on variations in the size of the ventricle, set scanning conditions based on the specified time phase, detect a period during which a volume variation indicating change in the size of the ventricle falls below a threshold value, and specify the detected period as the time phase of little cardiac motion, and
set the scanning conditions based only on the images obtained from the first preparatory scan; and
an imaging unit that performs one of coronary angiography and non-contrast angiography based on the set scanning conditions,
wherein the controller is configured to cause only the first preparatory scan to be performed, without causing other preparatory scans for specifying the time phase to be performed.

21. An X-ray Computed Tomography (CT) apparatus, comprising:
a controller configured to
obtain, from a first preparatory scan, images of a heart in each of a plurality of time phases, and cause additional cardiac imaging to be performed after the first preparatory scan,
measure sequential variations in a size of a ventricle within at least one heart beat, from the obtained images of the heart scanned in each of a plurality of time phases,
specify a time phase of little cardiac motion based on variations in the size of the ventricle, set scanning conditions based on the specified time phase, detect a period during which a volume variation indicating change in the size of the ventricle falls below a threshold value, and specify the detected period as the time phase of little cardiac motion, and
set the scanning conditions based only on the images obtained from the first preparatory scan; and
an imaging unit that performs coronary angiography based on the set scanning conditions,
wherein the controller is configured to cause only the first preparatory scan to be performed, without causing other preparatory scans for specifying the time phase to be performed.

22. The apparatus according to claim 21, wherein the controller is configured to set the scanning conditions such that a dose of X-rays to be irradiated to a subject when collecting data in a specified time phase is to be more than that when collecting data in other time phases within one heart beat.

23. The apparatus according to claim 22, wherein the controller is configured to set the scanning conditions such that a dose of X-rays to be irradiated to a subject when collecting data in the other time phases is to be zero.

24. The apparatus according to claim 21, wherein the controller is configured to use an image of a whole heart taken in a preparatory scan performed prior to a main scan by irradiating the heart with X-rays of a lower dose than that in the main scan.

25. The apparatus according to claim 21, wherein the controller is configured to use an image of a partial heart taken in a preparatory scan performed prior to a main scan by irradiating the heart with X-rays in an area narrower than that in the main scan.

* * * * *